United States Patent
Panzani et al.

(10) Patent No.: US 7,311,849 B2
(45) Date of Patent: Dec. 25, 2007

(54) CONTROL DEVICE FOR THE SEPARATE COLLECTION OF BLOOD COMPONENTS IN OUTPUT FROM A BLOOD CENTRIFUGATION CELL

(75) Inventors: Ivo Panzani, Mirandola (IT); Sergio Romagnoli, Castenaso (IT); Ivan Rossi, Poggio Rusco (IT); Stefano Sarti, Budrio (IT)

(73) Assignee: Sorin Group Italia S.r.l., Mirandola (MO) (IT)

( * ) Notice: Subject to any disclaimer, the term of this patent is extended or adjusted under 35 U.S.C. 154(b) by 530 days.

(21) Appl. No.: 10/898,720

(22) Filed: Jul. 23, 2004

(65) Prior Publication Data
US 2005/0054508 A1 Mar. 10, 2005

(30) Foreign Application Priority Data
Sep. 5, 2003 (IT) .......................... MI2003A1715

(51) Int. Cl.
 *B04B 13/00* (2006.01)
 *G01N 21/01* (2006.01)
(52) U.S. Cl. .................. 210/745; 210/94; 210/512.1; 210/787; 250/574; 250/576; 356/51; 356/435; 356/436; 494/1; 494/10; 494/37
(58) Field of Classification Search .................. 210/94, 210/96.1, 512.1, 745, 787; 494/1, 2, 10, 494/37, 43, 45; 356/39, 51, 433–436; 250/573–576
See application file for complete search history.

(56) References Cited

U.S. PATENT DOCUMENTS 3,096,283 A    7/1963  Hein
3,133,881 A    5/1964  Childs
3,145,713 A    8/1964  Latham, Jr. ............... 604/6.15
3,239,136 A    3/1966  Hein ........................... 494/1

(Continued)

FOREIGN PATENT DOCUMENTS

DE          26 58 926 A1      6/1978

(Continued)

OTHER PUBLICATIONS

U.S. Appl. No. 60/485,015, filed Jul. 2, 2003, Carter et al.*

(Continued)

*Primary Examiner*—Joseph Drodge
(74) *Attorney, Agent, or Firm*—Popovich, Wiles & O'Connell, P.A.

(57) ABSTRACT

The invention provides a control device for the separate collection of blood components in output from a blood centrifugation cell. The control device comprises: a support which comprises a recess for containing a duct; a visible-light emitter with a corresponding receiver, which are arranged on opposite sides with respect to the recess for containing the duct; an infrared-light emitter with a corresponding receiver, which are arranged on opposite sides with respect to the recess for containing the duct; and a processor to detect signals acquired by the two receivers, to calculate a ratio between the values of the signals, and to send signals to the means suitable to selectively send the fluid conveyed by the duct into separate collection bags, the means being able to change the bag in which the fluid is collected.

12 Claims, 2 Drawing Sheets

U.S. PATENT DOCUMENTS

| | | | |
|---|---|---|---|
| 3,244,362 A | 4/1966 | Hein | 494/1 |
| 3,244,363 A | 4/1966 | Hein | 494/1 |
| 3,456,875 A | 7/1969 | Hein | 494/3 |
| 4,069,968 A * | 1/1978 | Herman | 494/1 |
| 4,136,818 A * | 1/1979 | Larrabee | 494/1 |
| 4,142,670 A | 3/1979 | Ishimaru et al. | 494/38 |
| 4,199,544 A | 4/1980 | Muhlbock et al. | 494/16 |
| 4,402,680 A | 9/1983 | Schoendorfer | |
| 4,416,654 A | 11/1983 | Schoendorfer et al. | |
| 4,417,884 A | 11/1983 | Schoendorfer et al. | |
| 4,421,503 A | 12/1983 | Latham, Jr. et al. | |
| 4,447,220 A | 5/1984 | Eberle | |
| 4,530,691 A | 7/1985 | Brown | 494/45 |
| 4,646,167 A | 2/1987 | Denecke | |
| 4,683,579 A | 7/1987 | Wardlaw | |
| 4,724,317 A | 2/1988 | Brown | 356/28 |
| 4,734,089 A | 3/1988 | Cullis | 494/27 |
| 4,810,090 A | 3/1989 | Boucher et al. | |
| 4,944,833 A | 7/1990 | Belt et al. | |
| 4,946,434 A | 8/1990 | Plaisted et al. | |
| 4,983,158 A | 1/1991 | Headley | |
| 5,053,127 A | 10/1991 | Schoendorfer et al. | |
| 5,171,456 A | 12/1992 | Hwang et al. | |
| 5,234,608 A | 8/1993 | Duff | |
| 5,356,365 A | 10/1994 | Brierton | 494/14 |
| 5,368,542 A | 11/1994 | McMannis et al. | 494/45 |
| 5,494,592 A | 2/1996 | Latham, Jr. et al. | |
| 5,529,691 A | 6/1996 | Brown | |
| 5,545,516 A | 8/1996 | Wagner | |
| 5,565,977 A | 10/1996 | Rosinko | |
| 5,605,842 A | 2/1997 | Langley | |
| 5,607,579 A | 3/1997 | Latham, Jr. et al. | |
| 5,637,082 A | 6/1997 | Pages et al. | |
| 5,651,766 A | 7/1997 | Kingsley et al. | |
| 5,658,240 A | 8/1997 | Urdahl et al. | |
| 5,690,815 A | 11/1997 | Krasnoff et al. | |
| 5,722,946 A | 3/1998 | Mudloff et al. | |
| 5,728,306 A | 3/1998 | Breillatt, Jr. et al. | |
| 5,733,253 A | 3/1998 | Headley et al. | |
| 5,779,660 A | 7/1998 | Kingsley et al. | |
| 5,783,085 A | 7/1998 | Fischel | |
| 5,792,372 A | 8/1998 | Brown et al. | |
| 5,830,133 A | 11/1998 | Osten et al. | |
| 5,837,150 A | 11/1998 | Langley et al. | |
| 5,849,178 A | 12/1998 | Holm et al. | |
| 5,853,382 A | 12/1998 | Kingsley et al. | |
| 5,872,627 A | 2/1999 | Miers | |
| 5,876,611 A | 3/1999 | Shettigar | |
| 5,895,575 A | 4/1999 | Kraus et al. | |
| 5,936,714 A | 8/1999 | Gibbs | |
| 5,954,971 A | 9/1999 | Pages et al. | |
| 5,958,250 A | 9/1999 | Brown et al. | |
| 5,980,757 A | 11/1999 | Brown et al. | |
| 5,993,370 A | 11/1999 | Brown et al. | |
| 6,007,472 A | 12/1999 | Schill et al. | |
| 6,007,509 A | 12/1999 | Kingsley et al. | |
| 6,039,711 A | 3/2000 | Headley et al. | |
| 6,071,423 A | 6/2000 | Brown et al. | |
| 6,074,335 A | 6/2000 | Headley et al. | 494/26 |
| 6,099,740 A | 8/2000 | Holm et al. | |
| 6,102,883 A | 8/2000 | Kingsley et al. | |
| 6,106,727 A | 8/2000 | Krasnoff et al. | |
| 6,123,655 A | 9/2000 | Fell | |
| 6,144,444 A | 11/2000 | Haworth et al. | |
| 6,174,447 B1 | 1/2001 | Spindler | |
| 6,175,420 B1 | 1/2001 | Barry et al. | |
| 6,183,651 B1 | 2/2001 | Brown et al. | |
| 6,200,287 B1 | 3/2001 | Keller et al. | |
| 6,228,017 B1 | 5/2001 | Brown | |
| 6,231,537 B1 | 5/2001 | Holmes et al. | |
| 6,254,784 B1 | 7/2001 | Nayak et al. | |
| 6,284,142 B1 | 9/2001 | Muller | |
| 6,285,450 B1 | 9/2001 | Thomas et al. | |
| 6,296,602 B1 | 10/2001 | Headley | |
| 6,312,607 B1 | 11/2001 | Brown et al. | |
| 6,315,707 B1 | 11/2001 | Smith et al. | |
| 6,319,471 B1 | 11/2001 | Langley et al. | |
| 6,322,709 B1 | 11/2001 | Krasnoff et al. | |
| 6,325,775 B1 | 12/2001 | Thom et al. | |
| 6,348,156 B1 | 2/2002 | Vishnoi et al. | |
| 6,361,518 B1 | 3/2002 | Brierton et al. | |
| 6,379,322 B1 | 4/2002 | Kingsley et al. | |
| 6,409,696 B1 | 6/2002 | Toavs et al. | |
| 6,419,822 B2 * | 7/2002 | Muller et al. | 210/94 |
| 6,439,577 B2 | 8/2002 | Jorgensen et al. | 277/374 |
| 6,558,307 B2 | 5/2003 | Headley | |
| 6,602,179 B1 | 8/2003 | Headley et al. | 494/41 |
| 6,632,191 B1 | 10/2003 | Headley et al. | |
| 6,824,506 B1 | 11/2004 | Lamphere et al. | |
| 6,852,074 B1 | 2/2005 | Jorgenson et al. | 494/13 |
| 2002/0014462 A1 | 2/2002 | Muller | |
| 2002/0128585 A1 | 9/2002 | Cork et al. | |
| 2003/0191005 A1 * | 10/2003 | Coelho et al. | 494/37 |
| 2005/0051466 A1 * | 3/2005 | Carter et al. | 210/94 |
| 2005/0059540 A1 | 3/2005 | Skinkle et al. | |
| 2006/0021952 A1 | 2/2006 | Skinkle et al. | |

FOREIGN PATENT DOCUMENTS

| | | |
|---|---|---|
| WO | WO 87/06857 | 11/1987 |
| WO | WO 00/38762 | 7/2000 |
| WO | WO 01/03798 A1 | 1/2001 |

OTHER PUBLICATIONS

Dec. 14, 2004 Invitation to Pay Additional Fees and Partial International Search Report in PCT/US2004/029574 (7pages).

Mar. 31, 2005 Notification of Transmittal of the International Search Report and the Written Opinion of the International Searching Authority, or the Declaration in PCT/US2004/029574 (19 pages).

U.S. Appl. No. 11/079,940, filed Mar. 14, 2005, entitled Apparatus for Separating Blood Components.

U.S. Appl. No. 10/659,855, filed Sep. 11, 2003, for "Apparatus for Separating Blood Components", Skinkle et al.

Written Opinion of the International Searching Authority for International Application No. PCT/US2004/029574 (9 pages).

* cited by examiner

CONTROL DEVICE FOR THE SEPARATE COLLECTION OF BLOOD COMPONENTS IN OUTPUT FROM A BLOOD CENTRIFUGATION CELL

FIELD OF THE INVENTION

The invention relates to a control device in the separate collection of blood components in output from a blood centrifugation cell.

BACKGROUND OF THE INVENTION

It is known that one method for treating blood drawn from a patient that is currently performed includes introducing the blood to a cell, which is rotated so that by centrifugal force the blood components are separated according to their different density. In this manner, first plasma, then platelets, and finally red cells pass through the output duct of the cell. To perform separate collection of these components so that they are as pure as possible, i.e., not mixed with the others even in small quantities, it is obviously crucially important to know at all times the composition of the fluid that passes through the cell output duct and it is equally important to identify the moment when the command is to be sent to switch the bag into which the fluid conveyed by the cell output duct is to be directed.

The prior art proposes devices that are not entirely satisfactory, and it is therefore the aim of the present invention to provide a device that provides in an optimum manner the separate collection of the various blood components, particularly platelets, conveyed by the output duct of a blood centrifugation cell.

SUMMARY OF THE INVENTION

The proposed aim of the invention can be achieved by a control device for the separate collection of blood components in output from a blood centrifugation cell, the cell being connected by a duct made of soft and light-transparent material to means suitable to send selectively the fluid conveyed by the duct into bags for the separate collection of the individual blood components. The control device comprises: a support which comprises a recess for containing the duct; a visible-light emitter with a corresponding receiver, both of which are inserted in a first pair of aligned receptacles formed in the support and are arranged on opposite sides with respect to the recess for containing the duct; an infrared-light emitter with a corresponding receiver, both of which are inserted in a second pair of aligned receptacles formed in the support and are arranged on opposite sides with respect to the recess for containing the duct; and a processor to detect signals acquired by the two receivers, to calculate a ratio between the values of the signals, and to send signals to the means suitable to selectively send the fluid conveyed by the duct into separate collection bags, the means being able to change the bag in which the fluid is collected.

The invention also provides a method for the separate collection of blood components in output from a blood centrifugation cell comprising: (i) providing a blood centrifugation cell, the cell being connected by a duct made of soft and light-transparent material to means suitable to send selectively the fluid conveyed by the duct into bags for the separate collection of the individual blood components; (ii) providing a control device as described herein for the separate collection of blood components in output from a blood centrifugation cell; (iii) introducing blood into the blood centrifugation cell; (iv) centrifuging the blood; and (v) removing blood components from the blood centrifugation cell using the control device.

Additional features and advantages of the invention are set forth in the description which follows and in part will be apparent from the description. The objectives and other advantages of the invention will be realized and attained by the device as particularly pointed out in the written description and claims.

It is to be understood that both the foregoing general description and the following detailed description are exemplary and explanatory and are intended to provide further explanation of the invention as claimed.

BRIEF DESCRIPTION OF THE DRAWINGS

Further characteristics and advantages will become better apparent from the description of a preferred but not exclusive embodiment of the invention, illustrated by way of nonlimiting example in the accompanying drawings.

DETAILED DESCRIPTION OF THE PREFERRED EMBODIMENTS

Figure 1:
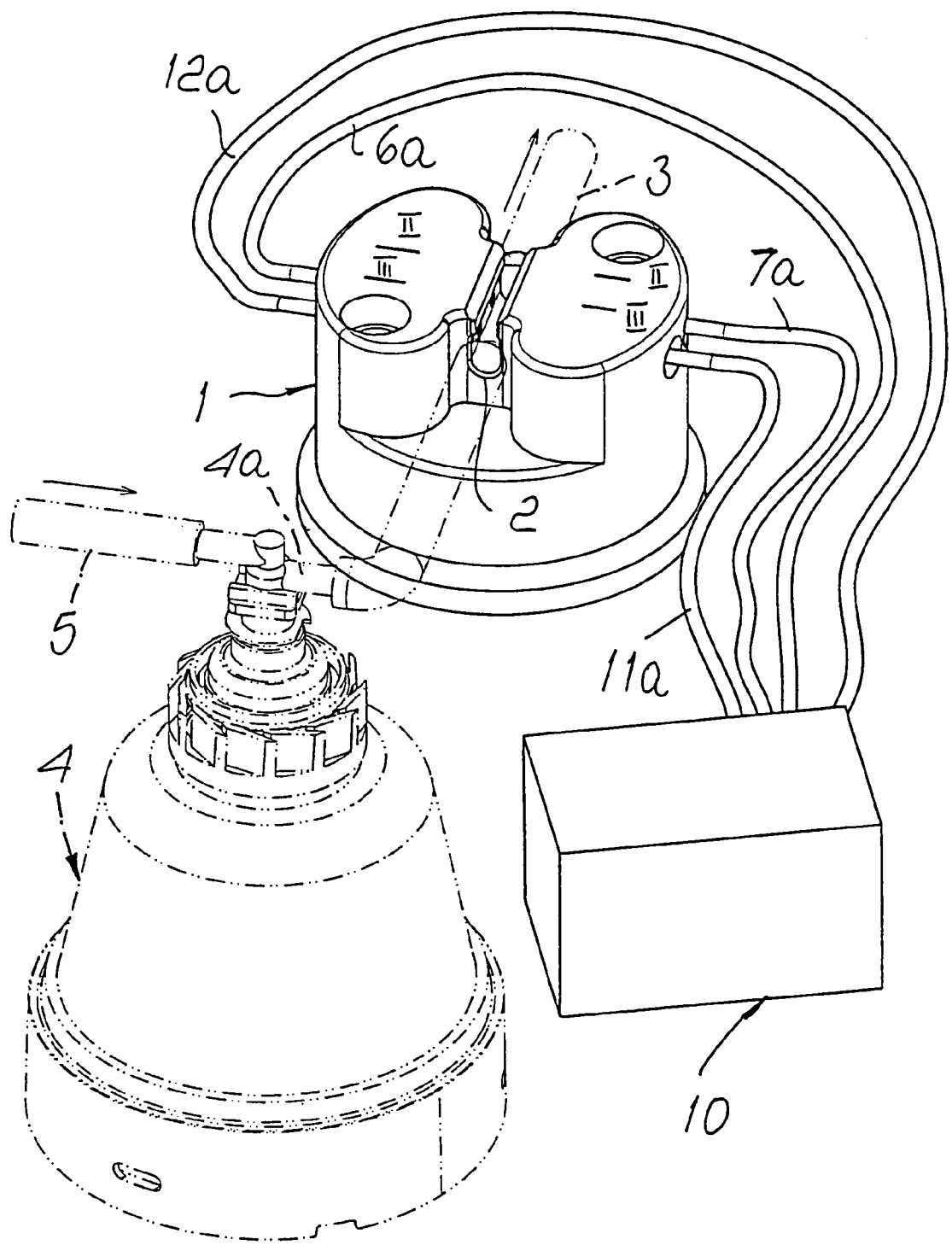
FIG. 1 is a general view of a control device of the invention, installed on the output duct of a centrifugation cell, shown by way of reference in dot-and-dash lines.

With reference to the figures cited above, the reference numeral 1 designates the support that comprises the recess 2 for accommodating the duct 3, which is made of soft and light-transparent material. The duct 3 is connected, at one end, to the output connector 4a of the cell 4 for performing centrifugation of blood that arrives from a patient by means of the line 5. The duct 3 is connected, at its other end, to means, not shown in the figure, that are suitable to send selectively the fluid conveyed by the duct into bags for the separate collection of the individual blood components. Therefore, first plasma, then platelets, and finally red cells will flow through the duct 3 to be sent into respective collection bags. Operation should be automatic, and therefore when plasma ceases to flow and be sent into a dedicated bag, it is necessary to send a first command that allows to collect the platelets that follow the plasma in an appropriately provided bag, and if one does not wish the platelets to be contaminated by the red cells that follow it is necessary to send a second signal that produces their collection in the bag dedicated to them.

Figure 2:
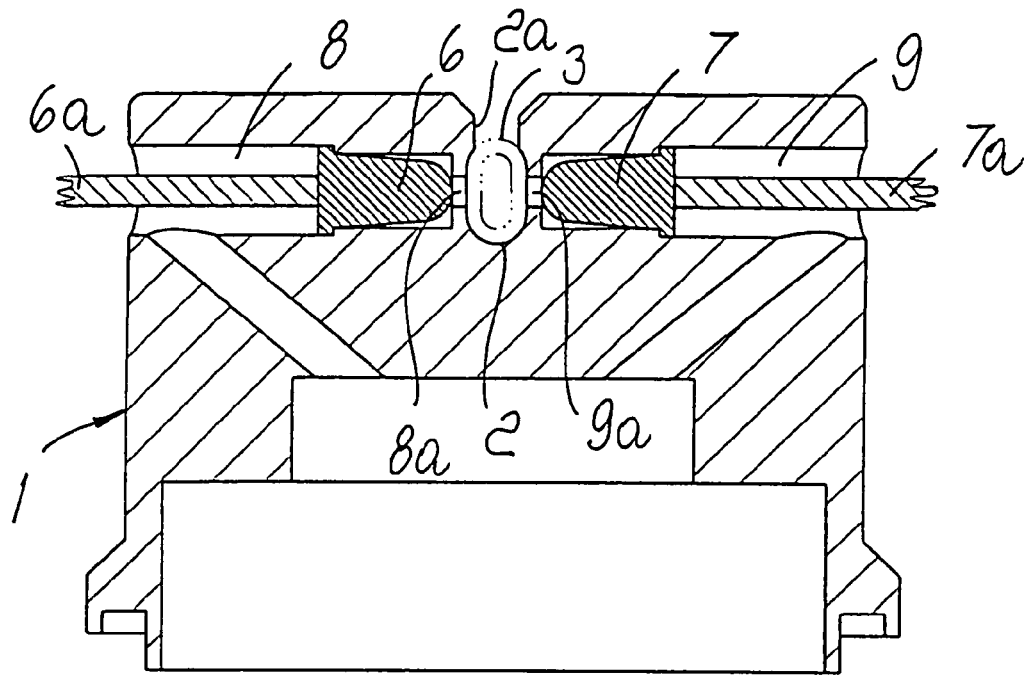
FIGS. 2 and 3 are sectional views, taken respectively along the planes II-II and III-III of FIG. 1.
Figure 3:
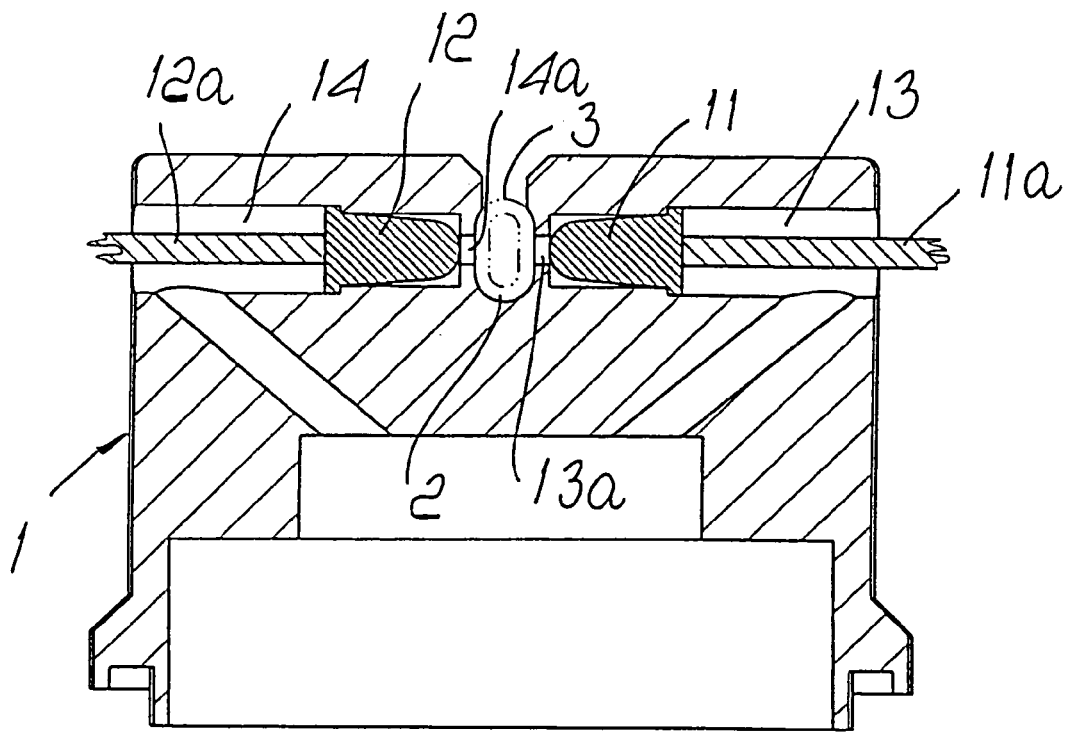

All this is provided by a control device of the invention shown in FIGS. 1 to 3, which comprises the emitter 6, which emits visible light at a wavelength of, for example, 570 nm, with a corresponding receiver 7. Visible light is light with a wavelength of from 780 nm to 380 nm. The emitter 6 and receiver 7 are inserted in two aligned receptacles 8 and 9 that are formed in the support 1. The receptacles 8 and 9 are arranged on opposite sides with respect to the recess 2, and lead into it through the holes 8a, 9a, which are smaller at the transverse axis of the recess, so as to ensure operation without problems caused by any interference produced by the wall of the duct 2 or by the presence of foam in the fluid conveyed by the duct. The emitter 6 and the receiver 7 are connected by the leads, designated by the reference numerals 6a and 7a respectively, to the control unit 10.

The control device of the invention shown in FIGS. 1 to 3 furthermore comprises the emitter 11, which emits infrared light at a wavelength of, for example, 950 nm, with a corresponding receiver 12. Infrared light is light with a wavelength of from 1 mm to 800 nm, but the shorter wavelengths within this range are the most useful for sensing applications. The emitter 11 and receiver 12 are inserted in the two aligned receptacles 13 and 14, which are located on opposite sides with respect to the recess 2 and lead into it by means of the small holes 13a and 14a. The emitter 11 and the receiver 12 are connected by the leads, designated by the reference numerals 11a and 12a respectively, to the control unit 10. The described placement of the emitters 6 and 11, located on opposite sides in the support 1, avoids any interference of the respective signals.

The control unit 10 comprises means suitable to detect the signals acquired by the two receivers 7 and 12, to calculate the ratio between the values of said signals, and to send signals to the means suitable to send selectively the fluid conveyed by the duct 3 into separate collection bags as described hereafter. At the beginning of the process, as mentioned, plasma flows in the duct 3, and absorbs in a substantially equal manner the visible light and the infrared light that passes through it and are emitted by the emitters 6 and 11 respectively. Accordingly, the light received by the receivers 7 and 12, respectively, and the signals sent to the control unit 10 are substantially identical and therefore the ratio between the values of the signals, processed by the control unit 10, is substantially equal to 1. All the plasma that flows is sent to the bag dedicated to the plasma.

After the plasma, platelets flow through the duct 3 and absorb visible light and infrared light in a slightly different manner. Since the absorption is slightly lower for infrared light, the light received by the receiver 12, which receives light emitted by the infrared-light emitter 11, is slightly greater than the light received by the receiver 7, which receives light emitted by the visible-light emitter 6. Operators can identify a value of the signal sent by the visible-light receiver that is typically indicative of the flow of platelets alone, and, therefore, when said value is reached the means comprised in the control unit 10 sends a signal that switches the bag to which the fluid conveyed by the duct 3 is sent. This new bag is the bag that is meant to collect platelets and remains connected to the duct 3 for all the time during which the platelets flow.

After the platelets, red cells flow through the duct 3 and absorb infrared light substantially less than visible light. Accordingly, when red cells begin to flow, the ratio between the values of the signals sent by the receivers 12 and 7, which are related respectively to infrared light and to visible light, begins to increase and increases rapidly as the concentration of the red cells increases. It is in any case possible to identify a value of the ratio that is typically indicative of the beginning of the flow of red cells in the duct 3, and when this value is reached the means comprised within the control unit 10 send a signal that sends the fluid conveyed by the duct into a new bag. This new bag collects the red cells.

Collection of the three blood components in separate bags with a high degree of purity has thus been achieved automatically. Before ending the description, it is noted that the recess 2 provided in the support 1 to accommodate the duct 3 has a narrower access portion 2a in order to produce uniform conditions for the insertion of the duct in the receptacle even if the duct is inserted in different manners, as may occur with different operators.

The above description and accompanying drawings are provided for the purpose of describing embodiments of the invention and are not intended to limit the scope of the invention in any way. It will be apparent to those skilled in the art that various modifications and variations can be made in the devices and methods without departing from the spirit or scope of the invention. Thus, it is intended that the present invention cover the modifications and variations of this invention provided they come within the scope of the appended claims and their equivalents.

What is claimed is:

1. A control device for the separate collection of blood components in output from a blood centrifugation cell, the cell being connected by a duct made of soft and light-transparent material to means suitable to send selectively the fluid conveyed by the duct into bags for the separate collection of the individual blood components, wherein the control device comprises:

a support which comprises a recess for containing the duct;

a visible-light emitter with a corresponding receiver, both of which are inserted in a first pair of aligned receptacles formed in the support and are arranged on opposite sides with respect to the recess for containing the duct;

an infrared-light emitter with a corresponding receiver, both of which are inserted in a second pair of aligned receptacles formed in the support and are arranged on opposite sides with respect to the recess for containing the duct; and a processor to detect signals acquired by the two receivers, to calculate a ratio between the values of the signals, and to send signals to the means suitable to send selectively the fluid conveyed by the duct into bags for the separate collection of the individual blood components, wherein the visible-light and infrared-light emitters, respectively, are inserted in the receptacles formed in the support on opposite sides with respect to the recess for containing the duct.

2. The device according to claim 1, wherein the processor sends a signal that is suitable first to switch the access of the fluid conveyed by the duct from a plasma collection bag to a platelet connection bag when the signal acquired by the visible-light receiver reaches a value that is typically indicative of the passage of only platelets in the duct, and then sends a signal that is suitable to switch the access of the fluid conveyed by the duct from the platelet collection bag to a red cell collection bag when the ratio between the values of the signals collected by the two receivers reaches a value that is typically indicative of the beginning of the flow of red cells in the duct.

3. The device according to claim 1, wherein the recess for containing the duct comprises a narrower access portion in order to produce uniform conditions for insertion of the duct.

4. The device according to claim 1, wherein the receptacles for the emitters and receivers comprise small holes adjacent to the recess in the support and each emitter and corresponding receiver are positioned along a transverse axis of the recess in the support, so as to avoid problems due to any interference produced by the wall of the duct or by the presence of foam.

5. The device according to claim 1, wherein the second pair of aligned receptacles are formed in the support proximate, with respect to the blood flow, to the receptacles of the first pair.

6. The device according to claim 1, wherein the second pair of aligned receptacles has the same shape as the first pair of aligned receptacles.

7. A method for the separate collection of blood components in output from a blood centrifugation cell comprising:

(i) providing a blood centrifugation cell, the cell being connected by a duct made of soft and light-transparent material to means suitable to send selectively the fluid conveyed by the duct into bags for the separate collection of the individual blood components;

(ii) providing a control device for the separate collection of blood components in output from a blood centrifugation cell, wherein the control device comprises:

a support which comprises a recess for containing the duct;

a visible-light emitter with a corresponding receiver, both of which are inserted in a first pair of aligned receptacles formed in the support and are arranged on opposite sides with respect to the recess for containing the duct;

an infrared-light emitter with a corresponding receiver, both of which are inserted in a second pair of aligned receptacles formed in the support and are arranged on opposite sides with respect to the recess for containing the duct; and a processor to detect signals acquired by the two receivers, to calculate a ratio between the values of the signals, and to send signals to the means suitable to send selectively the fluid conveyed by the duct into bags for the separate collection of the individual blood components, the means being able to change the bag in which the fluid is collected, wherein the visible-light and infrared-light emitters, respectively, are inserted in the receptacles formed in the support on opposite sides with respect to the recess for containing the duct;

(iii) introducing blood into the blood centrifugation cell;
(iv) centrifuging the blood; and
(v) removing blood components from the blood centrifugation cell using the control device.

8. The method according to claim 7, wherein the processor sends a signal that is suitable first to switch the access of the fluid conveyed by the duct from a plasma collection bag to a platelet connection bag when the signal acquired by the visible-light receiver reaches a value that is typically indicative of the passage of only platelets in the duct, and then sends a signal that is suitable to switch the access of the fluid conveyed by the duct from the platelet collection bag to a red cell collection bag when the ratio between the values of the signals collected by the two receivers reaches a value that is typically indicative of the beginning of the flow of red cells in the duct.

9. The method according to claim 7, wherein the recess for containing the duct comprises a narrower access portion in order to produce uniform conditions for insertion of the duct.

10. The method according to claim 7, wherein the receptacles for the emitters and receivers comprise small holes adjacent to the recess in the support and each emitter and corresponding receiver are positioned along a transverse axis of the recess in the support, so as to avoid problems due to any interference produced by the wall of the duct or by the presence of foam.

11. The method according to claim 7, wherein the second pair of aligned receptacles are formed in the support proximate, with respect to the blood flow, to the receptacles of the first pair.

12. The method according to claim 7, wherein the second pair of aligned receptacles has the same shape as the first pair of aligned receptacles.

\* \* \* \* \*